United States Patent [19]

Wells

[11] Patent Number: 4,574,729

[45] Date of Patent: Mar. 11, 1986

[54] CHAMBER BLOCK FOR A CYTOCENTRIFUGE HAVING CENTRIFUGAL FORCE RESPONSIVE SUPERNATANT WITHDRAWAL MEANS

[75] Inventor: John R. Wells, Culver City, Calif.

[73] Assignee: E. I. Du Pont de Nemours & Co., Wilmington, Del.

[21] Appl. No.: 637,782

[22] Filed: Aug. 6, 1984

[51] Int. Cl.[4] .............................................. B05C 11/08
[52] U.S. Cl. ........................................ 118/52; 118/264
[58] Field of Search ................. 118/264, 52; 604/904; 215/355

[56] References Cited

U.S. PATENT DOCUMENTS

| | | | |
|---|---|---|---|
| 1,116,663 | 11/1914 | Woodruff | 215/355 |
| 3,705,048 | 12/1972 | Staunton | 118/52 X |
| 3,738,364 | 6/1973 | Brien et al. | 604/904 X |
| 3,870,014 | 3/1975 | Buck | 118/52 |
| 3,999,549 | 12/1976 | Poncy et al. | 604/904 X |
| 4,103,643 | 8/1978 | Staunton | 118/50 |
| 4,108,109 | 8/1978 | Barger et al. | 118/52 |
| 4,197,329 | 4/1980 | Holroyd et al. | 427/2 |
| 4,241,005 | 12/1980 | Rothschild et al. | 118/52 X |
| 4,244,916 | 1/1981 | Guigan | 422/72 |
| 4,250,830 | 2/1981 | Leif | 118/52 |
| 4,391,710 | 7/1983 | Gordon | 210/361 |
| 4,423,699 | 1/1984 | Boeckel et al. | 118/52 |

OTHER PUBLICATIONS

Dore et al., National Institute for Medical Research, London, *Immunology*, 1965, 9, 403.

Watson, Taplow, Maidenhead, Berkshire, England, The Journal of Laboratory and Clinical Medicine, St. Louis, vol. 68, No. 3, pp. 494–501, Sep. 1966.

*Primary Examiner*—John P. McIntosh

[57] ABSTRACT

An arrangement for withdrawing supernatant from a deposition surface is provided for use with a cytocentrifuge chamber block. The block receives an absorbent plug in a recess provided therein. The plug is restrained from movement past a predetermined point until a predetermined insertion force corresponding to a predetermined rotor speed is imposed on the plug. At that time a resilient restraining arrangement deflects to permit the plug to advance with respect to the block. The restraining arrangement preferably takes the form of tines resiliently mounted to the plug.

4 Claims, 7 Drawing Figures

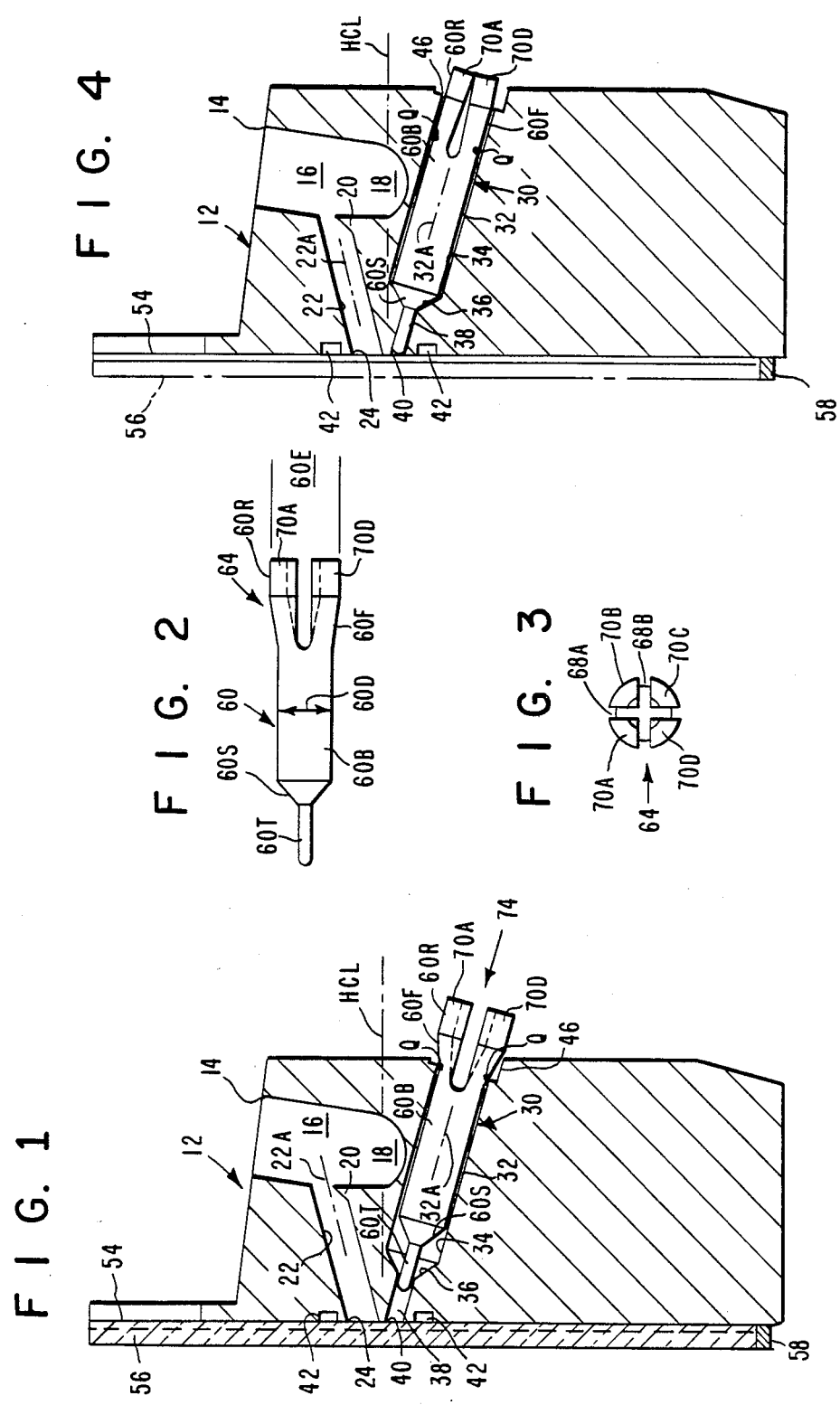

CHAMBER BLOCK FOR A CYTOCENTRIFUGE HAVING CENTRIFUGAL FORCE RESPONSIVE SUPERNATANT WITHDRAWAL MEANS

BACKGROUND OF THE INVENTION

This invention relates to a chamber block for use in a cytocentrifuge adapted to deposit particles suspended in a supernatant onto a deposition surface and, in particular, to a chamber block which is provided with a supernatant withdrawal system that is centrifugal force responsive.

Described in U.S. patent application Ser. No. 496,099, filed on May 19, 1983, is a chamber block for use in a cytocentrifuge which is adapted to sediment particles suspended in a liquid supernatant onto a deposition surface, such as a microscope slide. The chamber block includes an inlet orifice communicating with an inlet channel through which is introduced a sample of particles suspended in the supernatant. The inlet channel in turn communicates with an outlet channel that terminates in an outlet orifice disposed in adjacency to the deposition surface. When exposed to a centrifugal force field particles and supernatant move toward the deposition surface where the particles are sedimented thereon.

To facilitate the removal of excess supernatant the chamber block includes a recess, preferably in the form of a through-bore, that is adapted to receive an absorbent plug. The plug is fabricated, in the preferred instance, from porous polyethylene material. The bore and the plug are both correspondingly tapered over a predetermined portion of their length. When fully received within the bore the tip of the absorbent plug protrudes beyond the chamber block into contacting relationship against the deposition surface. During centrifugation the centrifugal force imposed on the supernatant overcomes the capillary force exerted by the absorbent material of the plug. As the rotor slows, however, the capillary force of the plug becomes dominant, thereby drawing the supernatant away from the deposition surface.

In practice, however, it has been found that while the centrifuge rotor rotates to its operating speed the presence of the absorbant plug in next adjacency to the deposition surface has the effect of prematurely withdrawing both supernatant and cells suspended therein. This is perceived as disadvantageous since it prevents the sedimentation of cells on the surface.

In view of the foregoing it is believed desirable to provide a mechanism which prevents the introduction of the plug into adjacency with the deposition surface until a predetermined operating speed is reached to thereby prevent premature wicking action of the plug.

SUMMARY OF THE INVENTION

In accordance with the present invention there is provided a centrifugal force responsive arrangement which restrains the movement of the absorbent plug with respect to a chamber block in which it is inserted into the region in adjacency to the deposition surface until the rotor reaches a predetermined operating speed. This operating speed corresponds to a predetermined centrifugal force. In the preferred embodiment of the invention the restraining arrangement takes the form of a deformable tine resiliently connected to the body portion of the absorbent plug. The deformable tine extends outwardly beyond the basic dimension of the plug to resist insertion of the plug past a predetermined distance into the recess of the chamber block toward the deposition surface until a predetermined rotor speed is achieved. When the predetermined rotor speed is reached, a centrifugally induced insertion force is imposed on the plug which causes the restraining arrangement to deform (i.e., the tine is deflected radially inwardly of the plug) and to permit the plug to displace with respect to the block toward the deposition surface.

In alternate embodiments the restraining means may be mounted within the body of the chamber block and may, for example, take the form of a detent which retracts in response to the insertion force imposed on the plug.

BRIEF DESCRIPTION OF THE DRAWINGS

The invention will be more fully understood from the following description thereof taken in connection with the accompanying drawings which form a part of this application and in which:

FIG. 1 is a side elevational view entirely in section of a cytocentrifuge chamber block having an absorbent plug disposed in the retracted position in a recess provided below the block's horizontal centerline;

FIGS. 2 and 3 are, respectively, elevational and end views of an absorbent plug shown in FIG. 1 having a restraining arrangement thereon in accordance with the present invention;

FIGS. 4 and 5 are views generally similar to FIG. 1 illustrating chamber blocks having with plug-receiving recesses respectively disposed below and above the horizontal centerline of the block with the absorbent plug shown in the protruding position with respect to the recess.

DETAILED DESCRIPTION OF THE INVENTION

Figure 5:
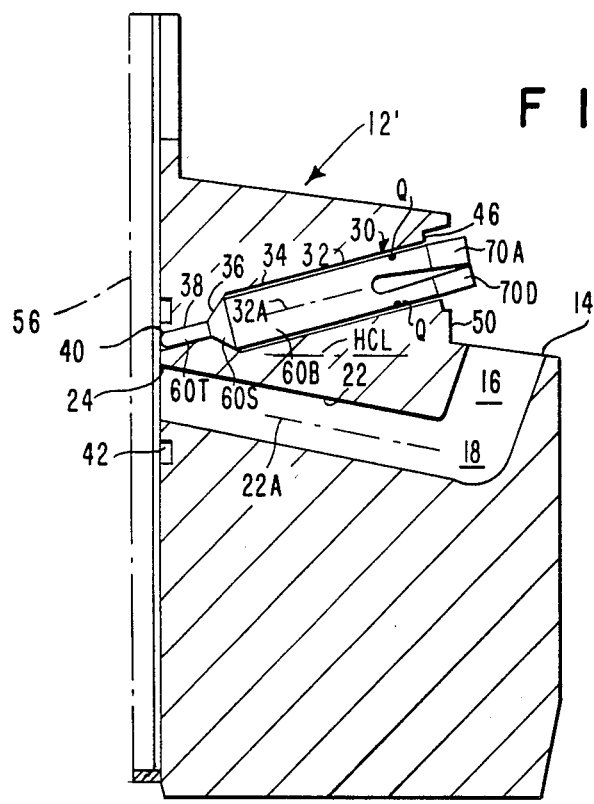

Throughout the following detailed description similar reference numerals refer to similar elements in all Figures of the drawings.

Shown in FIG. 1 is a chamber block 12 generally similar to that described in Application Ser. No. 496,099 referred to above. The block 12 is in the form of a generally rectangular member fabricated, as by injection molding, of any suitable material such as a polycarbonate plastic sold by General Electric Company under the trademark Lexan. The block has an inlet orifice 14 communicating with an inlet channel 16. A well region 18 is disposed at the lower end of the inlet channel 16. The inlet channel 16 communicates over a dam 20 with an outlet channel 22. The outlet channel 22 terminates in an outlet orifice 24. The dam 20 formed in the interior of the chamber block and is provided to prevent premature run-off of a sample of cells suspended in a supernatant which is introduced into the well 18.

The block 12 includes a recess 30 preferably in the form of a plug receiving bore 32 that extends from rear to front through that portion of the body of the chamber block 12 disposed below a reference horizontal centerline HCL. The bore 32 includes a generally cylindrical barrel portion 34, a tapered frustoconical shoulder portion 36, and a coaxial, narrower cylindrical portion 38. The opening 40 of the bore 32 lies on the front face of the block 12 within a predetermined close distance of the outlet orifice 24. The outlet orifice 24 and the opening 40 of the bore 32 are both surrounded by an annular groove 42 adapted to receive a suitable O-ring seal or the like (not shown). At the opposite, rear, face of the block 12 the entrance of the bore 32 is relieved, as at 46, to facilitate access to the bore 32.

The axis 32A of the bore 32 is inclined upwardly and together with the axis 22A of the outlet channel 22 subtends an angle in the range from ten to twenty degrees. However, in an alternate embodiment of the block 12' as shown in FIG. 5, the relative positions of the outlet channel 22 and the bore 32 may be reversed with respect to the reference horizontal centerline reference and remain within the contemplation of all aspects of this invention. As seen in FIG. 5, to accomodate the altered position of these features the contour of the block 12' is stepped, as at 50. Also, with the block 12' shown in FIG. 5 the dam 20 is eliminated.

The chamber block 12 carries a pair of vertically extending guide surfaces 54. The surfaces 54 cooperate to define a trackway in which a suitable deposition surface 56, such as a microscope slide, may be received. A slide stop 58 is disposed adjacent the lower end of the chamber block. The slide 56 may be secured to the block 12 by suitable clips (not shown). Otherwise the slide 56 may be retained between the block 12 and the periphery of the rotor in which they are disposed.

Referring to FIGS. 2 and 3, shown is a side elevational and rear view, respectively, of an absorbent plug 60 illustrating a restraining arrangement generally indicated by reference character 64 in accordance with one aspect of the present invention. The absorbent plug 60 is preferably an elongated substantially cylindrical member having a cylindrical body portion 60B which defines the basic dimension 60D of the plug 60. The forward end of the body 60B tapers through a frustoconical shoulder 60S to a coaxially projecting tip portion 60T. Trailing rearwardly from the body portion 60B is an outwardly flaring frustoconical section 60F which communicates to an enlarged coaxially disposed region 60R. The diameter 60E of the region 60R is greater than the diameter 60D of the body portion 60B of the plug 60. The plug 60 is fabricated of a material such as porous polyethylene and may be obtained, e.g., from Chromex Chemical Company, Brooklyn, N.Y.

In accordance with one embodiment of the invention, the restraining arrangement 64 is defined over the trailing sections of the plug 60 by the provision of axially extending crosscuts 68A, 68B which extend into the plug to approximately the point at which the section 60F tapers from the body 60B. The crosscuts 68A, 68B serve to define deformable tines 70A through 70D which are each resiliently movable or deformable toward the axis of the plug.

In operation, as seen from FIGS. 1 and 4, the plug 60 is initially introduced into the bore 32 until abutment between the block 12 and the points Q on each of the tines 70 is encountered and frictional forces between the plug 60 and the boundaries of the bore 32 prevent further manual insertion. The block 12 with the plug 60 introduced therein is then inserted into a rotor and rotated to speed. As the rotor reaches operative speed centrifugal force effects induce an insertion force acting in the direction of the arrow 74 which act on the plug 60. The centrifugally induced insertion force overcomes the frictional effects imposed on the tines 70 by the boundaries of the bore 32 and cause those tines 70 to deflect radially inwardly of the plug 60, thereby permitting the plug 60 to advance from the retracted position (shown in FIG. 1) to the protruding position (shown in FIG. 4). As a result, the protrusion of the tip 60T of the plug 60 through the opening 40 of the bore 32 is delayed until a predetermined rotor speed is reached. Similar action results in the tip 60T of the plug 60 protruding from the opening 40 of the embodiment of the block 12' shown in FIG. 5.

Figure 6:
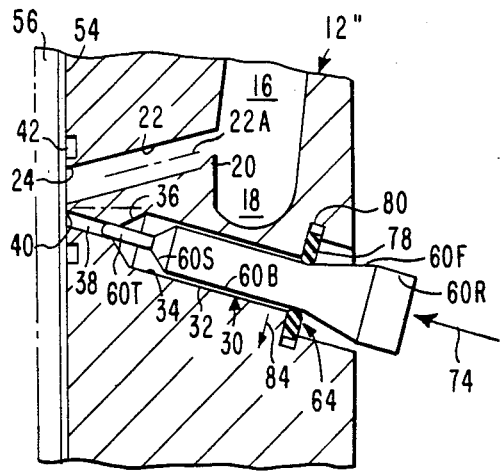
FIGS. 6 and 7 are elevational views similar to FIG. 1 illustrating an alternate embodiment in which the restraining arrangement is mounted within the chamber block and is respectively shown in the retracted and protruding positions.
Figure 7:
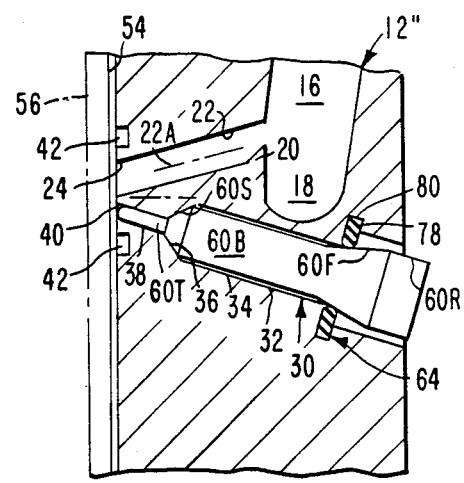

Alternatively, as shown in FIGS. 6 and 7 the restraining means 64 may take the form of a deformable detent ring 78 received within a corresponding groove 80 provided in the block 12'' circumferentially surrounding a portion of the bore 32. In this instance, the absorbent plug 60 is not provided with the crosscuts 68 as shown in FIGS. 2 and 3, but instead merely retains the enlarged diameter portion defined by the flaring region 60F and the enlarged coaxial cylindrical region 60R. This form of restraining means may, of course, also be used with a block 12' that provides the bore 32 above the reference horizontal centerline HCL.

In operation of this embodiment, the plug 60 is again introduced into the bore until forward movement thereof is restained by abutting engagement between the detent ring 80 and the flared region 60F of the plug 60. Thereafter, as the rotor moves to speed, the centrifugally induced insertion force 74 is imposed on the plug 60 to urge the detent ring 78 radially outwardly in the direction of arrows 84 to permit the plug 60 to move from the retracted position (FIG. 6) to the protruding position (FIG. 7). It should be understood that the detent, although shown in the form a resilient ring, may take any convenient form. For example, instead of groove 80, a channel may be formed within the body of the block to receive a spring biased detent ball which projects into the bore 32. Upon application of the insertion force to the plug the ball is urged against the bias of the spring into the channel to permit the plug to move to the protruding position.

In view of the foregoing, it may be appreciated that in accordance with this invention there has been provided a centrifugal force responsive restraining arrangement which delays the introduction of the tip of the plug into that vicinity of the deposition surface until sufficient centrifugal force or rotor speed has been reached. Thus, the supernatant withdrawal mechanism provided by the absorbent plug is made centrifugally force responsive and the disadvantages identified with the premature wicking action of the plug are eliminated.

Those skilled in the art, having benefit of the teachings of the present inventions hereinabove set forth, may effect numerous modifications thereto. However, such modifications are to be construed as lying within the scope of the present invention as defined by the appended claims.

What is claimed is:

1. A plug of absorbent material sized for insertion into a recess provided in a chamber block, wherein the plug comprises a substantially cylindrical member having a restraining arrangement thereon which resists introduction of the plug into the recess past a predetermined distance, the restraining arrangement comprising a flared portion at the trailing end of the plug, the flared portion extending radially of the plug to a point beyond the basic diameter of the plug, the plug having an axially extending cut provided therein to define a tine resiliently connected to the plug, the tine being deflectable radially inwardly of the plug in response to a circumferentially induced insertion force to permit further entry of the plug into the recess.

2. The plug of claim 1 wherein the plug has a pair of axially extending crosscuts provided therein to define a plurality of tines resiliently connected to the plug, each tine being deflectable radially inwardly of the plug in response to the insertion force.

3. A chamber block for a cytocentrifuge comprising:
   a body portion having an inlet channel adapted to receive a sample of cells suspended in a supernatant and an outlet channel terminating in an outlet orifice through which the cells and supernatant pass toward a deposition surface;
   the body portion having a recess therein, the recess being sized to receive and support a plug of absorbent material;
   a plug of absorbent material insertable within the recess to a first, retracted, position, the plug being movable with respect to the block from the first, retracted, to a second, protruding, position; and
   a restraining arrangement positioned with respect to the block and the plug to restrain movement of the plug past the retracted position, the restraining arrangement being mounted to the plug and comprises an array of tines resiliently connected to the plug, the tines flaring to a point beyond the basic dimension of the plug and which, in the first position, abuts against the body of the block, the tines being deflectable inwardly of the plug in response to a circumferentially induced insertion force to move the plug past the retracted to the protruding position as the plug and block are rotated at a predetermined rotational speed.

4. A chamber block for a cytocentrifuge comprising:
   a body portion having an inlet channel adapted to receive a sample of cells suspended in a supernatant and an outlet channel terminating in an outlet orifice through which the cells and supernatant pass toward a deposition surface;
   the body portion having a recess therein, the recess being sized to receive and support a plug of absorbent material, the block having a groove circumferentially disposed with respect to and communicating with recess;
   a plug of absorbent material insertable within the recess to a first, retracted, position, the plug being movable with respect to the block from the first, retracted, to a second, protruding, position; and
   a restraining arrangement mounted within the block, the restraining arrangement comprising a detent engagable with the plug to prevent movement of the same past the retracted position, the detent being deflectable in response to the action of a circumferentially induced insertion force on the plug to permit the plug to move past the retracted position to the protruding position as the plug and the block are rotated at a predetermined rotational speed.

* * * * *